United States Patent [19]

Dawson

[11] 4,348,181
[45] Sep. 7, 1982

[54] RETAINING DEVICE FOR A REMOVABLE DENTAL PROSTHESIS

[75] Inventor: Peter E. Dawson, St. Petersburg, Fla.
[73] Assignee: Ipco Corporation, White Plains, N.Y.
[21] Appl. No.: 237,919
[22] Filed: Feb. 25, 1981
[51] Int. Cl.³ .............................................. A61C 13/22
[52] U.S. Cl. .................................................... 433/172
[58] Field of Search ............................... 433/177, 172
[56] References Cited

U.S. PATENT DOCUMENTS 3,057,067 10/1962 Morandi ............................... 433/172

FOREIGN PATENT DOCUMENTS 513785 2/1955 Italy .................................... 433/172

Primary Examiner—Robert Peshock
Attorney, Agent, or Firm—Friedman, Goodman & Teitelbaum

[57] ABSTRACT

A retaining device for removably securing a dental prosthesis in position, having a fixed male section for securement to the side of a fixed tooth and a cooperating free female section for securement within the dental prosthesis. The male section includes a projection which is received in an inverted U-shaped housing at the forward end of the female section. A spring loaded plunger member positioned within the female section extends into the housing and engages a recess formed in the projection thereby locking the two sections together. A jig is provided for suitably placing spaced apart male sections in alignment and in proper parallel relationship.

16 Claims, 7 Drawing Figures

RETAINING DEVICE FOR A REMOVABLE DENTAL PROSTHESIS

BACKGROUND OF THE INVENTION

This invention relates to a removable dental prosthesis, and more particularly to a device for securing such removable dental prosthesis in the mouth.

There are various dental prostheses which are placed in the mouth and while they must be fixed in position, at the same time appropriate devices must be provided to permit their removal when desired. For example, partial dentures or removable bridge work are inserted in the mouth and must be securely held in place. At the same time, they occasionally need to be removed for cleaning and maintenance. Nevertheless, while they are in the mouth, they must be retained sufficiently secured to the natural teeth to prevent displacement during use.

Numerous holding devices of the above type have been known in the art. For example, U.S. Pat. No. 3,089,242 describes a device where a ring is attached to the dental prosthesis and is slid downward into a channel which is secured into the side of a fixed tooth. U.S. Pat. No. 3,380,161 describes a detent mechanism inserted in an artificial tooth which engages a recess formed in an adjacent natural tooth. Another such detent mechanism is described in U.S. Pat. Nos. 3,304,610 and 2,748,480.

While each of the aforementioned devices provides an appropriate mechanism for retaining a dental prosthesis, the ability to provide improved retention of the dental prosthesis while at the same time facilitating removal thereof, can be improved upon over prior art devices.

SUMMARY OF THE INVENTION

Accordingly, it is an object of the present invention to provide an improved device for retaining a removable dental prosthesis in the mouth.

Another object of the present invention is to provide securing means for a removable dental prosthesis which makes the accidental displacement or removal of the prosthesis so unlikely that the securing means is completely reliable.

A further object of the present invention is to provide a retaining device for a removable dental prosthesis which gives it a more life-like or more natural feeling in the mouth and yet permits removability of the prosthesis.

Still another object of the present invention is to provide a retaining device for a removable denture which secures the prosthesis with a natural resiliency and at the same time may be quickly and easily removed.

Still another object of the present invention is to provide a retaining device for removably securing a dental prosthesis, which facilitates securement of the device in order to insure its stability.

A further object of the present invention is to provide a retaining device for a removable dental prosthesis which permits easy replacement of the parts of the device.

Still another object of the present invention is to provide a retaining device for securing a dental prosthesis which permits easy insertion of the device in the removable and fixed parts of the teeth and assures suitable alignment and parallelism of the parts.

Yet a further object of the present invention is to provide a retaining device for removably securing a dental prosthesis which can be easily placed using a suitable jig.

Another object of the present invention is to provide a jig which can be used in conjunction with sections of a retaining device in order to insert the device, position it properly and achieve both parallelism and alignment.

Briefly, in accordance with the present invention, there is provided a retaining device for removably securing a dental prosthesis in position. The device includes a fixed male section which is secured to a side of a fixed tooth, and a cooperating free female section for securement within the dental prosthesis. The female section includes an elongated casing with a spring loaded plunger member disposed within the casing with the plunger member projecting therefrom. Included within the female section are suitable arrangements for limiting the extent of longitudinal travel of the plunger member within the casing. The male section includes a securing mechanism for fixedly retaining the male section in place on the fixed tooth. It also includes a recessed member for cooperatively receiving the projecting plunger member to thereby anchor the dental prosthesis to the fixed tooth.

The recessed member includes a projecting block from the male section and in which a recess is formed for receiving the plunger member. On the female section, in turn, there is provided a housing which extends from the casing and receives the projecting block. In this manner, the projecting block forming the recessed member is actually inserted within a housing, and the plunger member which extends into the housing is received within the recess in the recessed member.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying draiwings of a preferred embodiment in which.

In the various figures of the drawing, like reference characters designate like parts.

DETAILED DESCRIPTION OF THE PREFERRED EMBODIMENT

Figure 1:
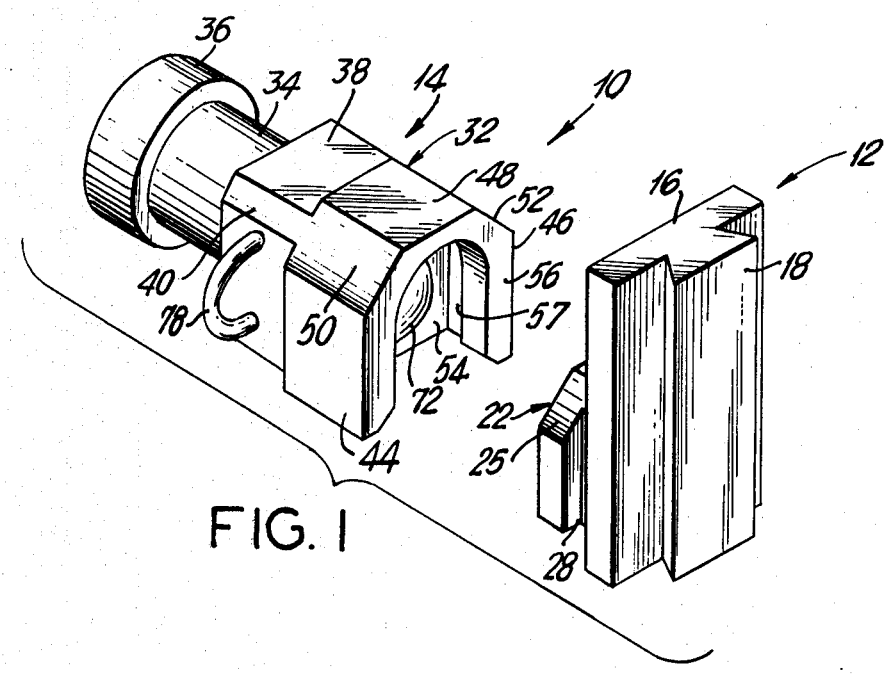
FIG. 1 is a perspective view of the male and female sections of the retaining device, unassembled, in accordance with the present invention.
Figure 2:
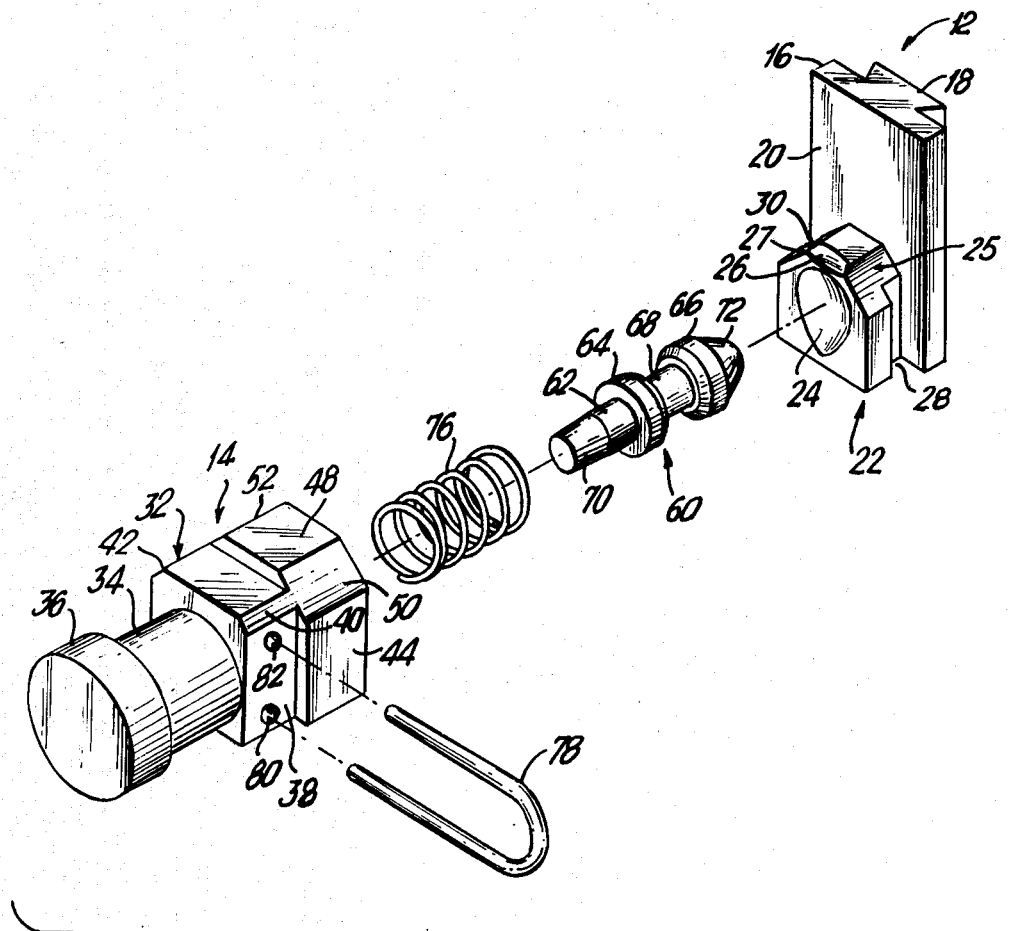
FIG. 2 is an exploded view of the various parts forming the retaining device as shown in FIG. 1.
Figure 3:
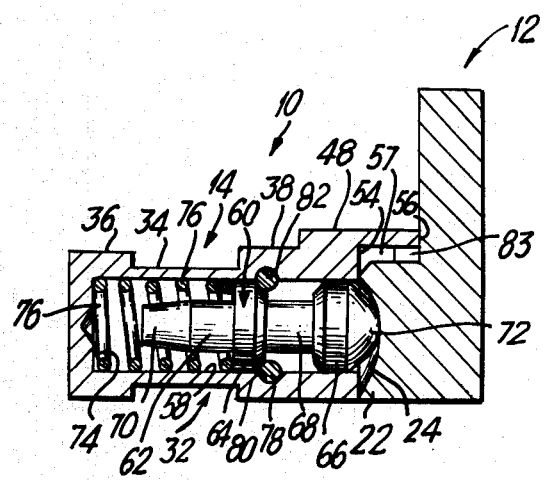
FIG. 3 is an elevational sectional view taken through the retaining device when the two male and female sections thereof are in an assembled, engaged position.

Referring now to FIGS. 1-3, the retaining device is shown generally at 10 and comprises a fixed male section 12 which is to be secured to the side of a fixed tooth, and a cooperating free female section 14 to be secured in the dental prosthesis. The male section 12 includes a solid rectangular plate 16 from which extends toward the rear a dovetail spline 18. The height of the spline 18 extends the entire height of the plate 16. Protruding from the front face 20 of the plate 16, and extending only from the lower half thereof, is a projecting block 22 which constitutes a recessed member, the block 22 having a narrower width than the plate 16. Formed into the projecting block 22 is a recess 24, and above the recess 24 is provided a cam surface 26 formed as a cut out at the upper edge of the block 22. The upper edge and sides of the block 22 are tapered or beveled to provide beveled surfaces 25, 27. On either side of the block 22 there is provided undercut channels 28, 30 for receiving a portion of the female section 14, as will hereinafter be explained.

The female section 14 includes a casing shown generally at 32 which is formed of various sections including a cylindrical section 34 from which extends an enlarged circular flange at its base 36. Forward of the cylindrical section 34 is a block section 38 having tapered or beveled surfaces 40, 42 at its upper corners. At the front of the casing there is provided a larger section which is provided with a substantially inverted U-shaped portion including the side sections 44, 46 and the upper section 48. The three sections 44, 46 and 48 are interconnected by tapered or beveled sections 50 and 52. It should be noted that the front portion is hollow and includes an open bottom. The front facing 54 within the hollow of the front portion is spaced from the outer front face 56 of the female section 14, with the side walls of the hollow being undercut at 57 adjacent to the front facing 54, as can best be seen in FIG. 1.

As is noted in FIG. 3, a longitudinal bore 58 extends from the front facing 54 of the female section 14 inwardly through the various sections of the casing 32 and into the rear collar section or base 36. Positioned within the bore 58 is a plunger member, shown generally at 60. The plunger member 60 includes a cylindrical body section 62 along which is positioned two enlarged circular collar sections 64, 66, spaced apart from each other to define a neck section 68 therebetween. It should be noted that the collar sections have beveled edges facing toward the intermediate neck section 68. The rear 70 of the body section 62 is slightly tapered. Forward of the collar 66 is a front end having a conical projection 72.

A coil spring 76, having closed end loops at both ends thereof, is mounted into the rear of the bore 58 and extends between the back end 74 of the bore 58 and the first collar 64 of the plunger member 60. The body portion 62 of the plunger member together with the tapered rear section 70, extend into the center of the coil spring 76.

The plunger member 60 is held in place within the case 32 by means of a U-shaped wire clip or brad 78 which is inserted into the spaced apart receiving holes 80, 82 which extend through the section 38 so that the holes extend into the bore 58. The spacing between the holes 80, 82 is less than the diameter of the bore 58 so that the legs of the wire clip 78 extend into the bore 58 and are disposed around the neck portion 68 of the plunger member. The plunger member 60 is thus captured within the casing 32 but is free to axially move within the bore 58 a distance corresponding to the length of the neck section 68. The collars 64, 66 will abut against the legs of the wire clip 78, thus defining the limit of the axial movement of the plunger member. The length of the plunger member is such that is extends forward of the casing facing 54 and into the space defined by the inverted U-shaped portion at the front of the casing 32.

When assembled as shown in FIG. 3, the projecting block 22, extending forward of the plate 16 of the male section 12, is received within the inverted U-shaped portion at the front of the casing 32, with the undercuts 28, 30 of the block 22 and the undercuts 57 within the hollow of the casing 32 providing a tongue and groove engagement to prevent relative rotation therebetween. The plunger member 60 extends into the recess 24 formed in the projecting block 22 to secure the sections 12 and 14 together.

The parts are arranged so that the male section 12 can initially be secured to the side of a fixed tooth, and the female section 14 will then be inserted into the dental prosthesis. The two sections 12 and 14 are first located so that they are adjacent to each other, and then the dental prosthesis carrying the section 14 is vertically moved downward into position. The housing at the front of the casing 32 will then move onto the projecting block 22, being guided by the tapered surfaces 25 and 27 to position the projecting block 22 within the inverted U-shaped housing with the above mentioned tongue and groove engagement therebetween. At the same time, the plunger member 60 will be guided by means of the cam surface 26 into the recess 24 provided in the projecting block 22. The assembled parts can best be seen in FIG. 3.

It should be noted that the projecting block 22 on the male section 12 is situated within the inverted U-shaped housing of the female section 14, and the plunger member 60 is situated within the recess 24. The spring 76, biasing the plunger member, holds the plunger member tightly within the recess 24 and locks the projecting block 22 within the housing of the female section 14. Accordingly, a secure locking arrangement is provided. However, it should also be noted that there is slight vertical movement permitted by means of the plunger member which can move vertically within the recess 24, the projecting block 22 being smaller than the height of the housing hollow and accordingly provides a clearance 83. This clearance 83 permits the prosthesis containing the female section 14 to be pressed against the gum for the approximation of a feeling of elasticity of a living bone in the human mouth, so that the prosthesis, when inserted in the mouth, more nearly feels like natural teeth to the wearer. At the same time, the holding device provides a secure engagement which prevents wobble and provides the necessary security to hold the dental prosthesis in place, wherein the plunger member 60 will seat itself in the recess 24 in the position shown in FIG. 3 when there is no applied pressure on the prothesis.

The prosthesis can be removed by pulling upward on the prosthesis. This upward pull will force the conical surface 72 of the forward end of the plunger member 60 to move inward of the casing 32 as it is pulled upward in the recess 24. The movement inwardly of the plunger member 60 releases the engagement between the male section 12 and the female section 14, and allows the dental prosthesis to be removed.

Figure 4:
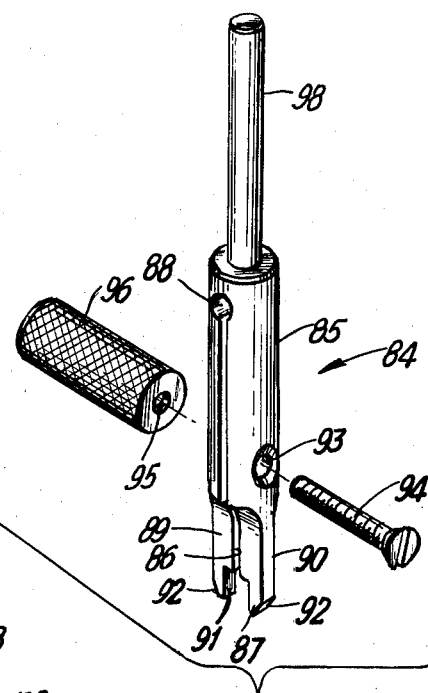
FIG. 4 is an exploded perspective view of a jig useful in inserting the male section of the retaining device of the present invention.

In order to accurately position a pair of the male sections 12, there is provided a jig which is designed to securely hold the male sections 12, one at a time, so as to accurately align them in parallelism. Referring now to FIG. 4, it will be noted that the jig 84 is formed of a cylindrical body member 85 having an axially extending diametric slot 86 formed therethrough. The slot 86 commences from the free end 87 of the jig 84 and extends to almost the upper end of the cylindrical body member 85 to divide the body member 85 into two joined sections which are slightly spaced apart. The slot termintes in an enlarged bore 88 where the two sections are joined. The forward end of the cylindrical body is flattened to provide front and rear surfaces 89, 90. Additionally, a U-shaped channel 91 is formed at the free end 87 which enlarges the elongated slot 86 at the front end. The depth of the channel 91 is such as to accommodate the height of the projecting block 22, as will hereinafter be described. The outside edges of the free end 87 are tapered or beveled at 92.

A diametric bore 93, substantially perpendicular to the elongated slot 86, is formed through the cylindrical body member 85. A screw 94 passes through the bore 92 and threads into a threaded hole 95 in a knurled knob 96. As the knurled knob 96 is tightened onto the screw 94, the two sections or legs of the cylindrical member 85, which are separated by the elongated slot 86, are brought together. In this manner, the bottom portions of the two sections or legs separated by the channel 91 can be moved closer together so as to form a clamp at the free end 87 to retain one of the male sections 12 of the holding device therebetween, as will hereinafter be explained.

Figure 5:
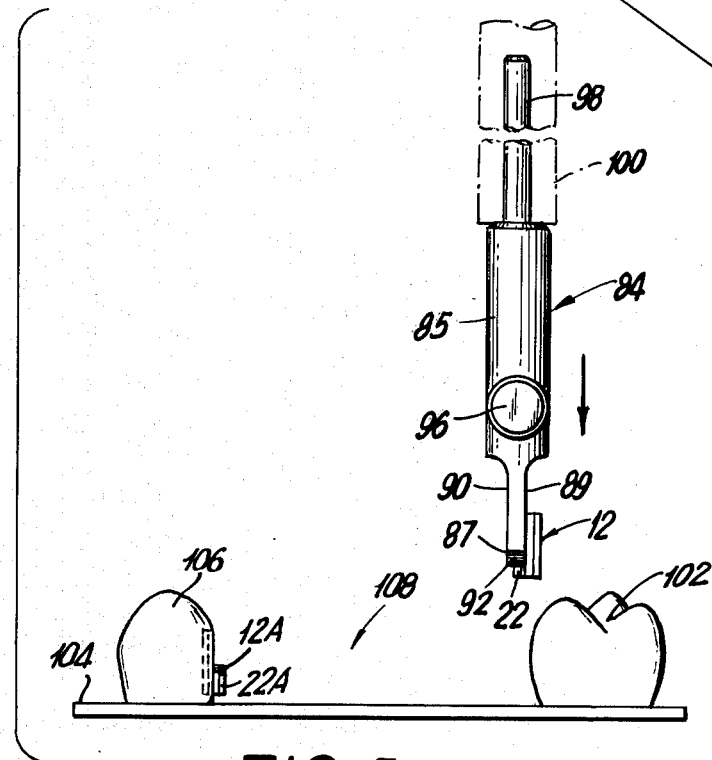
FIGS. 5 and 6 show steps in the placement of the retaining device when utilizing it in conjunction with a dental prosthesis.

As shown in FIG. 5, the jig 84, as heretofore described in connection with FIG. 4, grasps the male section 12 by having the spaced apart legs formed by the channel 91 at the lower end of the jig 84 grasp the opposite sides of the projecting block 22, with the edges of the wider plate 16 abutting against either of the body surfaces 89 or 90, and the block 22 disposed in the channel 91. With the knob 96 tightened, the male section 12 will be held securely within the jig 84. By means of a suitable parallel tool 100, well known in the art, attached to the shank portion 98 of the jig body member 85, the jig 84 can suitably wax the male section 12 in place adjacent the cast tooth model 102 of the patient's teeth. Such cast model is formed by well known methods and is positioned on a holding plate 104. A corresponding male section 12A is already shown waxed in place on the cast tooth model 106, wherein the tool 100 positions the sections 12, 12A so that they are parallel to each other. A crown will then be cast in the usual manner from the teeth models 102, 106, including the male sections 12, 12A therein, so that the male sections 12, 12A will be formed within the crown. It should be noted that the projecting blocks 22, 22A will extend forward from the side of the crown.

Figure 6:
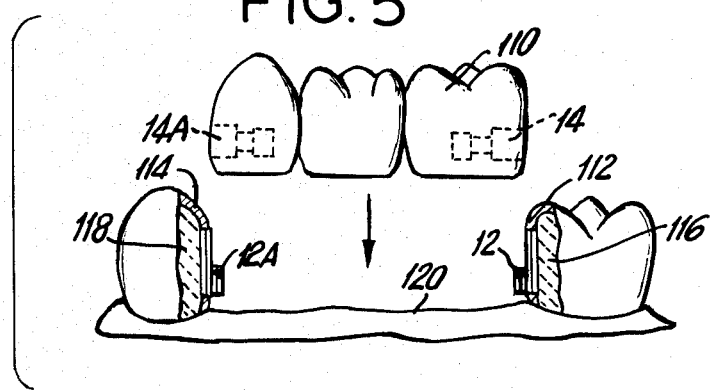

Within the free space 108 between the male sections 12, 12A, there is formed a suitable dental prosthesis, in accordance with standard techniques. For example, as shown in FIG. 6, a bridge 110 has been formed for insertion between the existing teeth. It should be noted, that within the prosthesis 110 when cast, is included the female sections 14 and 14A which have been suitably positioned by attachment to the male sections 12, 12A, respectively, when the prosthesis 110 was being formed.

Once the crowns 112, 114 have suitably been cast from the teeth models 102, 106, the crowns are positioned in place on the actual teeth 116, 118, which have previously been prepared, as shown in FIG. 6. The male sections 12 and 12A will thus be secured directly to the actual teeth 116, 118 positioned in the mount. The dental prosthesis 110 can then be inserted onto the gum 120 and positioned between the existing teeth 116, 118 so that the female sections 14, 14A will lock onto the male sections 12, 12A as heretofore described.

Figure 7:
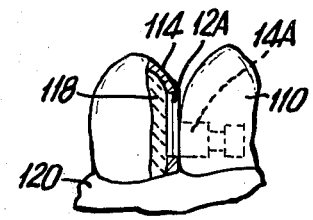
FIG. 7 is a partially broken away elevational view showing the positioning of the sections of the retaining device between removable and fixed teeth in the mouth area.

Referring now to FIG. 7, there is shown in more detail the actual tooth 118 having the crown 114 thereon with the male section 12A engaging the female section 14A which in turn is secured into the portion of the dental prosthesis 110. It is noted, that the spline 18 of the male section 12 functions to secure the male member in the crowns 112, 114, and the configuration of the casing 32 of the female section 14 functions to secure the female member in the dental prosthesis 110.

More particularly, in placing the sections, the model is initially surveyed to determine the correct position of the male section 12, 12A. The goal is to keep the male section 12, 12A within the normal contour of the tooth yet maintain its maximum length. The male sections 12, 12A are then placed into the jig 84 one at a time, the jig being secured to the conventional parallelometer. The male sections 12, 12A are then waxed within a recess in order to properly receive the female sections 14, 14A. The male sections 12, 12A are waxed into place while still being held in the parallelometer.

Conventionally, a Bard Parker blade is placed on top of the male section 12 or 12A being worked on. The jig is then removed while counteracting the friction force with opposite pressure on the Bard Parker to prevent dislodging of the male section 12 or 12A being worked on. The waxing of the male sections 12, 12A are then completed to proper contour.

The casting is then processed in the conventional manner including the steps of providing the sprue and investing. The investment is then burnt out and the cast of the crown is made. When the crown is complete with the male sections 12 and 12A in place, the female sections 14, 14A are inserted into the male sections 12, 12A and the two sections secured together. An impression of the entire master model is taken and the denture casting or prosthesis 110 is constructed in the conventional manner. The dental casting 110 is then placed on the master model and secured to the back portion of the female sections 14, 14A either with plaster or wax. This procedure is used in order to obtain the proper relationship for soldering the denture casting 110 to the female sections 14, 14A.

It is noted, that should the plunger member 60 of the female section 14 fail to function properly, the plunger member 60 can be removed from the female section 14 without removing the female section 14 from the prosthesis 110. Accordingly, the bight of the U-shaped clip 78 is first located or found in the prosthesis 110, and the clip 78 is then removed from the female section 14 by pulling on the bight thereof. Once the clip 78 is removed, the plunger member 60 can be removed from the bore 58. Thus, the plunger member 60 and the spring 76 can be replaced in the female section 14. The new plunger member 60 is first held in the bore 58 and the clip 78 is then reinserted into the holes 80, 82. One of the legs of the clip 78 is longer than the other, so that the longer leg is first inserted into one of the holes 80, 82 to act as a guide for inserting the shorter leg into the other hole. The hole, which was made in the prosthesis 110 in order to locate the clip 78, is then filled in in a conventional manner well known in the art.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A retaining device for removably securing a dental prosthesis in position, said device comprising, in combination, a male section for securement to a side of a fixed tooth, and a cooperating female section for securement within the dental prosthesis, said female section including an elongated casing, said male section including a projecting member receivable in said casing, a spring loaded plunger member disposed in said casing and projecting therefrom, first means within said casing for limiting the extent of longitudinal travel of said plunger member, said male section including securing means for fixedly retaining said male section in place on the fixed tooth, said projecting member including second means for cooperatively receiving said plunger member to thereby anchor the dental prosthesis to the fixed tooth, and third means coacting between said casing and said projecting member to prevent relative rotation between said male and female sections, said plunger member including an elongated cylindrical body portion, longitudinally spaced apart enlarged first and second collars on said body portion defining a neck portion therebetween, said first collar being at a forward end of said plunger member, said casing including an elongated bore extending therein and having a closed inner end, said plunger member being disposed in said bore, and a biasing spring being disposed in said bore, said spring being biased between said closed inner end and said second collar, said first means including a restricting member in said casing for engaging both said first and second collars to capture said plunger member within said casing and to limit its longitudinal movement, said restricting member including a wire clip removably inserted through an opening in a side wall of said casing and extending transversely into said bore adjacent said neck portion in a position between said first and second collars.

2. A retaining device as in claim 1, wherein said wire clip includes two legs connected by a bight to define a U-shape, said legs being disposed on opposite sides of said neck portion, said bight being positioned outside said casing.

3. A retaining device as in claim 2, wherein one of said wire clip legs is longer than the other leg to act as a guide for inserting said other leg into said casing.

4. A retaining device as in claim 1, wherein said body portion of said plunger member extends partially into said biasing spring.

5. A retaining device as in claim 1, wherein said casing includes a body portion, an enlarged foot portion at one end thereof for assisting in securement of said casing within the dental prosthesis, and a forward head portion at an opposite end thereof, said forward head portion having flat sides thereabout to prevent rotation within the dental prosthesis.

6. A retaining device as in claim 1, wherein said second means includes a recess provided in said projecting member of said male member for accommodating said plunger member.

7. A retaining device as in claim 6, wherein said projecting member includes a cam surface vertically positioned above said recess to guide said plunger member into said recess.

8. A retaining device as in claim 6, and further including vertical undercuts laterally provided in opposite sides of said projecting member to receive vertical undercut portions of said casing to provide a tongue and groove engagement therebetween to define said third means for preventing relative rotation.

9. A retaining device for removably securing a dental prosthesis in position, said device comprising, in combination, a male section for securement to a side of a fixed tooth, and a cooperating female section for securement within the dental prosthesis, said female section including an elongated casing, said male section including a projecting member receivable in said casing, a spring loaded plunger member disposed in said casing and projecting therefrom, first means within said casing for limiting the extent of longitudinal travel of said plunger member, said male section including securing means for fixedly retaining said male section in place on the fixed tooth, said projecting member including second means for cooperatively receiving said plunger member to thereby anchor the dental prosthesis to the fixed tooth, third means coacting between said casing and said projecting member to prevent relative rotation between said male and female sections, said casing including a forward head portion having an inverted U-shaped housing therein for receiving said projecting member of said male section, internal side walls of said housing and external side walls of said projecting member being undercut to provide a tongue and groove engagement therebeween to define said third means for preventing relative rotation.

10. A retaining device as in claim 9, wherein said male section includes a plate, said projecting member extending from one side of said plate, said securing means including a dovetailed spline extending from an opposite side of said plate.

11. A retaining device for removably securing a dental prosthesis in position, said device comprising, in combination, a male section for securement to a side of a fixed tooth, and a cooperating female section for securement within the dental prosthesis, said female section including an elongated casing, said male section including a projecting member receivable in said casing, a spring loaded plunger member disposed in said casing and projecting therefrom, first means within said casing for limiting the extent of longitudinal travel of said plunger member, said male section including securing means for fixedly retaining said male section in place on the fixed tooth, said projecting member including second means for cooperatively receiving said plunger member to thereby anchor the dental prosthesis in the fixed tooth, third means coacting between said casing and said projecting member to prevent relative rotation between said male and female sections, and a jig for positioning said male section on said side of the fixed tooth, said jig including an elongated cylindrical body, a longitudinally extending diametric slot in said cylindrical body extending from a free end thereof and splitting said cylindrical body into a pair of bifurcated legs, free ends of said legs having a flattened front and rear side, a channel provided at said free ends of said legs to widen a portion of said slot at said free ends by a sufficient distance to grasp therebeween said male section of said retaining device, and clamping means for clamping said bifurcated legs together.

12. A retaining device in combination with a jig as in claim 11, wherein said clamping means includes a diametric hole formed through said legs substantially perpendicular to said slot, and a clamping screw extending through said hole for tightening said legs together.

13. A retaining device in combination with a jig as in claim 11, and further comprising a shank extending from said cylindrical body for coupling to a positioning tool.

14. A device for retaining a removable dental prosthesis, comprising, in combination, a first member for securement to a fixed tooth, a projection extending from said first member, a second member for securement within the dental prosthesis, a housing extending from said second member for receiving said projection, retaining means for releasably retaining said projection within said housing, engaging means to prevent relative rotation between said first and second members, said retaining means including a spring biased plunger member projecting into said housing and a recess provided in said projection for receiving and retaining said plunger member therein, said housing having substantially an inverted U-shape in cross section so that said housing can vertically slide over and receive said projection therein, said projection including vertical undercuts provided on opposite external sides thereof and said housing having vertical undercut portions on opposite internal walls thereof to provide a tongue and groove engagement therebetween to define said engaging means to prevent relative rotation.

15. A device as in claim 14, wherein said projection further includes a cam surface vertically positioned above said recess for guiding said plunger member into said recess.

16. A device for retaining a removable dental prosthesis, comprising, in combination, a first member for securement to a fixed tooth, a projection extending from said first member, a second member for securement within the dental prosthesis, a housing extending from said second member for receiving said projection, retaining means for releasably retaining said projection within said housing, and engaging means to prevent relative rotation between said first and second members, and a jig for positioning said first member on the fixed tooth, said jig having an elongated body, said elongated body having a longitudinal slot extending from a free end thereof to define a pair of bifurcated legs, an inverted U-shaped grasping section at free ends of said bifurcated legs to provide a widened portion of said slot for grasping said projection of said first member between said bifurcated legs, and clamping means for tightening said bifurcated legs together.

* * * * *